United States Patent
Babtsov et al.

(10) Patent No.: US 7,045,546 B2
(45) Date of Patent: May 16, 2006

(54) STABILIZED DERIVATIVES OF ASCORBIC ACID-3-PHOSPHATE

(75) Inventors: Vladimir Babtsov, Kiryat Shmona (IL); Yury Shapiro, Givat Shmuel (IL); Emma Kvitnitsky, Kiryat Shmona (IL); Valery Belakhov, Haifa (IL)

(73) Assignee: Tagra Biotechnologies Ltd., Netanya (IL)

(*) Notice: Subject to any disclaimer, the term of this patent is extended or adjusted under 35 U.S.C. 154(b) by 0 days.

(21) Appl. No.: 10/484,689

(22) PCT Filed: Jul. 26, 2001

(86) PCT No.: PCT/IL01/00690

§ 371 (c)(1), (2), (4) Date: Jul. 15, 2004

(87) PCT Pub. No.: WO03/010173

PCT Pub. Date: Feb. 6, 2003

(65) Prior Publication Data

US 2004/0242544 A1    Dec. 2, 2004

(51) Int. Cl.
*A61K 31/375* (2006.01)
*C07D 307/62* (2006.01)

(52) U.S. Cl. .................. 514/474; 514/844; 549/315; 549/317

(58) Field of Classification Search ........... 549/315, 549/317
See application file for complete search history.

(56) References Cited

U.S. PATENT DOCUMENTS 3,671,549 A * 6/1972 Hinkley .................... 549/222

FOREIGN PATENT DOCUMENTS

| DE | 1805958 | 5/1969 |
| DE | 1668743 | 3/1972 |
| DE | 3613590 | 11/1985 |
| EP | 0875248 | 11/1998 |

* cited by examiner

*Primary Examiner*—Bernard Dentz
(74) *Attorney, Agent, or Firm*—Browdy and Neimark, PLLC

(57) ABSTRACT

Novel derivatives of ascorbic acid and compositions comprising them are provided. The novel derivatives are of the following general formula (I): where R1 is a C2–C22 saturated or unsaturated fatty acid residues, amino acid residues, or a C1–C17 alkyl ; R2 is a group of the following formula (II) wherein R5 or R6 are the same or different and represent hydrogen, a C1–C4 alkyl, or R5 is C1–C4 alkyl group and R6 is a metal cation or ammonium cation; R3 or R4 are the same or different and represent hydrogen, C2–C22 saturated or unsaturated fatty acid residues, amino acid residues, or a C1–C17 alkyl.

21 Claims, 1 Drawing Sheet

STABILIZED DERIVATIVES OF ASCORBIC ACID-3-PHOSPHATE

This application is a national stage entry of PCT/IL01/00690 filed Jul. 16, 2001.

1. Field of the Invention

This invention relates to the new ascorbic acid derivatives and pharmaceutical and cosmetic compositions containing them.

2. Prior Art

The following references are considered to be relevant in illustrating the state of the art in the field of the invention:

EP 306,904, U.S. Pat. Nos. 5,098,904, 3,671,549, JP 63,104,971, JP 7,017,989, JP 8,034,791, JP 98,363,316, JP 98,201,242, JP 10,324,672, DE 3,613,590 and DE 1,805,958.

BACKGROUND OF THE INVENTION

L-Ascorbic acid, widely known in its generic name Vitamin C, is used in pharmaceuticals, food additives and cosmetics. It is widely used in connection with its antioxidative properties. The formulation of pure vitamin C into an end product, however, is difficult since it is oxidized easily, especially in aerobic conditions and upon light exposure. Therefore, rather than using ascorbic acid in its pure form, typically its derivatives are used. Ascorbic acid in its lactone form has four hydroxyl groups at carbons 2, 3, 5 and 6. These hydroxyl groups have different chemical activity. The 2- and 3-hydroxyl groups form an enediol system together with the double bond connecting carbons 2 and 3, which is very sensitive to oxidation. This system accounts to the oxidative degradation of ascorbic acid. The 5- and 6-hydroxyl groups on the other hand form a rather stable diol system. Common derivatization of ascorbic acid converts the hydroxyls to alkyl, acyl, sulfo or phospho-containing groups, which also influence the solubility of ascorbic acid in water or in oils. Known ascorbic acid derivatives fall into two main groups: water-soluble and oil-soluble ascorbic acid derivatives. These two groups differ in their potential use.

Widely used topical formulations contain 6-ascorbyl palmitate or stearate, fatty acid esters and thus have lipophilic properties and 2- or 3-magnesium ascorbyl phosphate, inorganic water-soluble acid esters. The enediol system of 6-ascorbyl palmitate is unprotected and this derivative is unstable in aqueous systems. It also has a rather limited solubility in water, oils and solvents commonly used in topical formulations. The enediol systems with the 2- or 3-ascorbyl phosphates and 2,3-di-O-acylates are relatively protected but may also become oxidized. Furthermore, they usually have to be produced in their polar, salt form, which is not compatible for skin formulations.

It was hitherto found that ascorbic acid and its derivatives up-regulate expression of procollagen genes in cultured dermal fibroblasts. It is well known that the collagen and elastin syntheses are mediated through lipoperoxides or their oxidative responses. The products of oxidation of ascorbic acid glycate proteins and rapidly produce protein-bound adducts and protein cross-links. The rate of glycation depends on oxidation rate of ascorbic acid in tissue. It is very important that oxidation begins only after penetration into stratum corneum, but not earlier. This means that ascorbic acid must be derivatized in order to prevent early oxidation. In this case ascorbic acid and its derivatives are able to stimulate collagen and elastin syntheses and significantly improve the condition of epidermis as well as corium of the skin tissue.

In recent years significant steps have been made to introduce vitamins and other active agents into dermatological or cosmetic compositions. These compositions may be used for specific treatments of various skin problems such as aging, dryness, acne or pigmentation disorders. Vitamin C incorporated into various compositions has to be strongly protected against oxidation by formulation, storage when formulated and by skin treatment.

EP 306,904 describes another approach in the field of vitamin formulation, involving binding of vitamin derivatives to a carrier. An example for a carrier is phosphoric acid to which two vitamin derivatives are bound, e.g. an ascorbic acid derivative and a tocopherol derivative, yielding an anti-oxidant composition. However, in this bi-vitamin form, the vitamin derivatives display a lower efficacy than in a free form. U.S. Pat. No. 5,098,898 describes the coupling of glycerol ester or ether to L-ascorbic acid via a phosphoric acid residue. The resulting compound exhibits good anti-oxidant activity as well as lipid peroxide inhibiting activity. However the enediol system is not adequately protected and thus cannot be used as a source of vitamin C in topical formulations.

JP 63,104,971 and DE 3,613,590 disclose synthesis of 2,3-di-O-acyl L-ascorbic acids, which are more photostable than above-mentioned phosphorylated L-ascorbic acids. However, 2,3-di-O-acylation leads to the loss of a biological activity and bioaccessibility because the low solubility of product in water. Therefore, such compounds are practically useless for cosmetic, dermatological and other applications.

JP 7,017,989, JP 8,034,791, JP 98,363,316 and JP 98,201,242 disclose applications of L-ascorbyl-2-phosphate in chemical peeling and skin-whitening compositions to prevent penetration of the agents to skin in depth and reduce skin irritation. 2-Phosphate containing derivatives of L-ascorbic acid show appropriate stability and preserve own activity.

U.S. Pat. No. 3,671,549 and DE 1,805,958 disclose synthesis of L-ascorbyl-3-phosphate by direct phosphorylation of ascorbic acid with a phosphorus halide, phosphoric and halophosphoric acids and corresponding anhydrides. The process is suitable for large-scale use.

JP 10,324,627 discloses synthesis of the L-ascorbic acid derivatives having phosphate, pyrophosphate, triphosphate, polyphosphate, sulfate, or glycosyl groups in position 2, and OH, phosphate, polyphosphate, sulfate, glycosyl, alkoxyl, alkenyloxyl, or phenoxyl groups in position 3, for their application as antitumor drugs. The problem of stability was not an aim of this patent but the new pharmacological activity only. Therefore position 2 was not o-substituted with the residue effective enough for the oxidative protection of the enediol double bond.

SUMMARY OF THE INVENTION

The present invention provides compounds of the general formula (I):

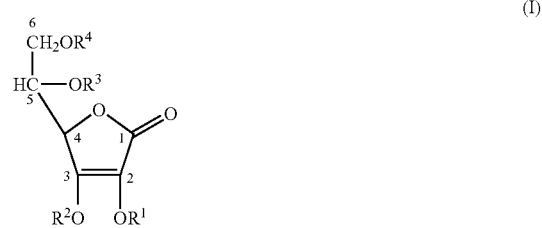

wherein $R^1$ is a $C_2$–$C_{22}$ saturated or unsaturated fatty acid residues, an amino acid residues, or a $C_1$–$C_{17}$ alkyl; $R^2$ is a group of the following formula (II):

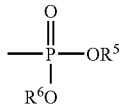

(II)

wherein $R^5$ and $R^6$ are the same or different and represent hydrogen or a $C_1$–$C_4$ alkyl, or $R^5$ is $C_1$–$C_4$ alkyl group and $R^6$ is a metal cation or ammonium cation; and $R^3$ and $R^4$ are the same or different and represent hydrogen, $C_2$–$C_{22}$ saturated or unsaturated fatty acid residues, amino acid residues, or a $C_1$–$C_{17}$ alkyl.

The compounds of formula (I) above are useful for inclusion in cosmetic or pharmaceutical compositions (hereinafter, collectively: "vitamin C compositions"). Thus, provided by the invention, and in accordance with another of its aspects are pharmaceutical or cosmetic compositions comprising the compound of formula (I) together with a pharmaceutical or cosmetic applicable carrier, excipient or diluent. A preferred composition in accordance with the invention is a topical composition for skin application. In addition, vitamin C compositions in accordance with the invention may also be at times formulated for oral administration. As will be appreciated, the vitamin C compositions of the invention may include a variety of other ingredients, e.g. a pharmaceutical or a cosmetic active ingredient. The ascorbic acid may be included in the compositions of the invention for its anti-oxidative properties. At times, however, the vitamin C composition of the invention may have the main purpose of delivery of the vitamin C derivative of formula (I).

In accordance with yet another aspect of the invention there is provided a process for synthesis of a compound of formula (I), comprising the following steps:

(i) protecting the 5' and 6' hydroxyls of the ascorbic acids, by reacting ascorbic acid with a ketone of the general formula $R^7R^8CO$, wherein $R^7$ and $R^8$, which may the same or different, represent a $C_1$–$C_{10}$ alkyl, to yield a compound of the general formula (III):

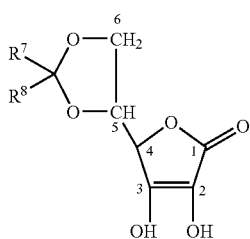

(III)

(ii) reacting the resulting protected ascorbic acid molecule of formula (III) with a compound of the general formula $R^1H$, wherein $R^1$ has the above meanings, to yield a compound of general formula (IV):

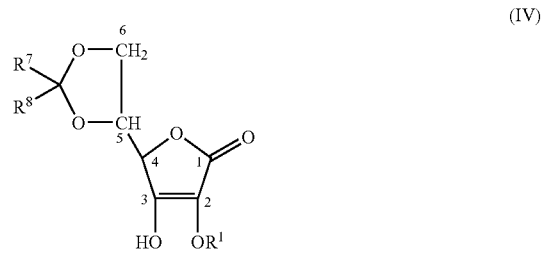

(IV)

(iii) reacting the compound of formula (IV) with a mixture of phosphorous oxide chloride and the salt $R^6$—O—Z; wherein $R^6$ is as defined above and Z is an alkaline metal cation, to yield a compound of formula (V):

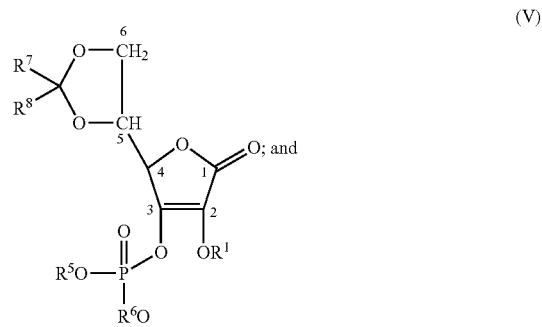

(V)

(iv) hydrolyzing the compound of formula (V) to deprotect the 5- and 6-hydroxyls, to yield the compound of the general formula (I).

DETAILED DESCRIPTION OF THE INVENTION

As stated above, the present invention provides derivatives of ascorbic acid of formula (I):

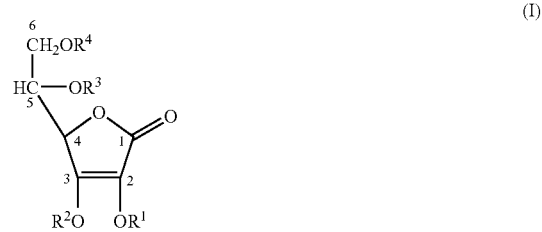

(I)

wherein $R^1$, $R^2$, $R^3$ and $R^4$ have the above meanings.

These derivatives are more stable as compared to ascorbic acid. The stability of these derivatives stems from the fact that simultaneous derivatization of the 2- and 3-hydroxyls protects the 2- and 3-enediol system. At the same time, the derivatives of formula I serve as reliable, versatile and effective source of ascorbic acid to human tissues in need thereof. These compounds serve, following their hydrolysis in situ, by enzymes present in tissue such as skin, as a source of phosphates, carbon acids or amino acids. In order to achieve a relatively high percentage of liberated ascorbic acid after hydrolysis, the overall molecular weight of the compounds of formula I should be kept rather low. Thus preferably, although not essentially, no derivatization is needed for the 5-and 6-hydroxyls as these groups are rather stable and derivatization may unnecessarily increase the molecular weight of the ascorbic acid derivative. Such an increase in molecular weight may decrease the amount of liberated ascorbic acid per unit weight of compound. At times, however, such increase in molecular weight may be beneficial.

In order for the compounds to serve as the biologically accessible source of ascorbic acid, the $R^1$, $R^2$, $R^3$ or $R^4$ are each independently chosen from natural and physiologically compatible moieties such as saturated and unsaturated fatty acids, amino acids and phosphoric acid derivatives.

The fatty acids may be, but are not limited to, caprylic, palmitic, oleic, linoleic, linolenic, arachidonic acids. Enzymes in tissue such as those of skin cells could easily hydrolyze such derivatives and all the hydrolysis products are natural compounds and may thus have a physiological significance. Furthermore, they have a moderate polarity thus may be soluble in both aqueous and lipophilic media.

Compounds of formula (I) may be used in cosmetic and dermatological compositions for an effective delivery of vitamin C to the skin. Furthermore, the compounds of the invention may also be formulated for oral administration. For topical administration the compositions may be prepared in various forms including, but not limited to, gels, ointments, salves, liquids, etc. For oral administration the compounds of the invention may be formulated in capsules, microcapsules or nanoparticles, tablets or liquids. The nature of the formulation may vary depending on the intended use and depending on the overall polarity of the specifically used compound of formula (I). For example, a polar compound of formula (I) may be formulated in an aqueous formulation such as a gel, while a more hydrophobic compound of formula (I) may be formulated in an emulsion form. In tablets, for example, the active ingredient is mixed with a carrier having the necessary compression properties in suitable proportions and compacted into the shape and size that is desired. Solid carriers include, for example, calcium phosphate, magnesium stearate, talc, sugars, lactose, dextrin, starch, gelatin, cellulose, methylcellulose, sodium carboxymethyl cellulose and polyvinylpyrrolidine. Liquid formulations include, for example, suspensions, emulsions or syrups. Liquid carriers include, for example water, organic solvents, mixtures of pharmaceutically acceptable oils or fat and others. Suitable liquid carriers for oral administration are, for example, water, alcohols, and oils.

The compositions of the invention comprise an effective amount of a compound of formula I. The effective amount is an amount of the compound that is needed in order to achieve a desired therapeutic or cosmetic effect. The effective amount may thus depend on the desired therapeutic or cosmetic effect, on the condition to be treated, on the state of the condition, on the gender of the treated subject, on his sex or age, on the administration regiment on the nature of the compound of formula I, etc. A person versed in the art should be able by limited and routine experiments to determine the effective amount in each case.

The synthesis of the 2,3-substituted derivatives has to be done in a manner so as not to disrupt the 2- and 3-enediol system.

Compositions containing compounds of formula (I) show good delivery of ascorbic acid to cells (in vitro). They may thus be used for this purpose. The compositions of the invention may also be used to treat diseases disorders, or conditions that are associated with ascorbic acid deficiency in cells or tissue or such diseases, disorders or conditions that may be ameliorated by the delivery of ascorbic acid to cells or tissue. There are also a variety of cosmetic applications where supplementation of ascorbic acid may have a beneficial effect.

The invention will now be illustrated by the following non-limiting examples.

EXAMPLES

Example 1

Synthesis of 2-caproyl-3-ethyl(calcium)phosphoryl ascorbic acid

Figure 1:
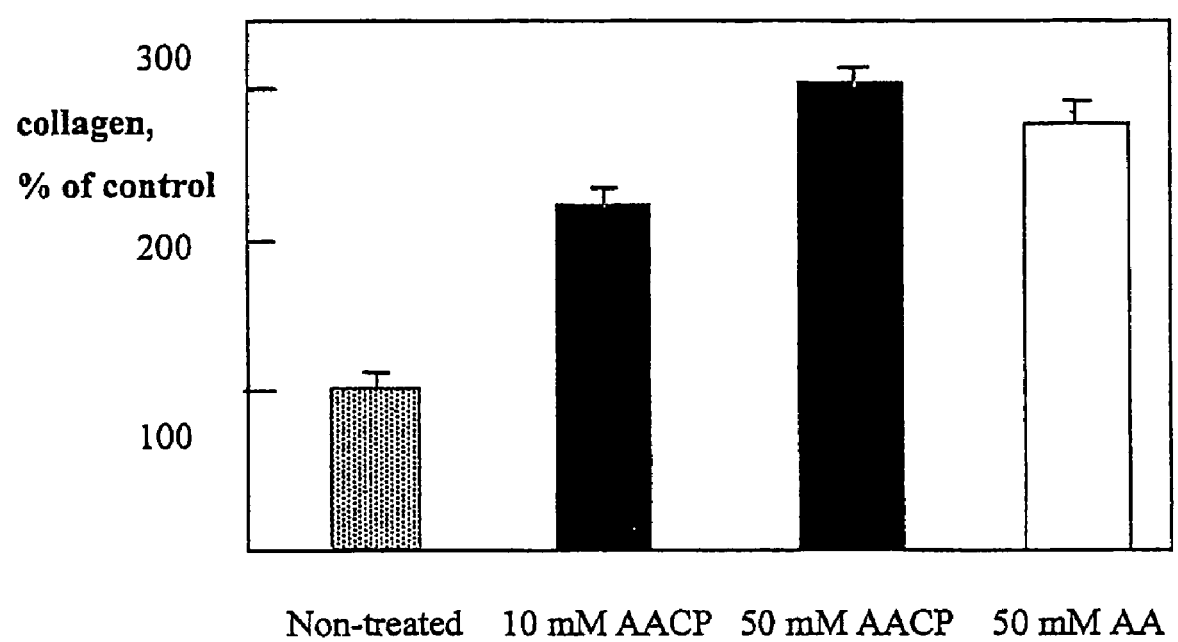
FIG. 1 in the drawing shows a bar-graph representation of results of an experiment in which the amount of collagen, represented as percent of control (control=100%) as a function of exposure of ascorbic acid (AA) or different concentrations of 2-caprilate 3-monoethylphosphate (AACP) is shown.

Step 1. Synthesis of 5,6-isopropylidene ascorbic acid.

20 g (0.125 mol) of anhydrous cupric sulfate were added to a suspension of 20 g (0.114 mol) of ascorbic acid in 660 mL of dry acetone. The reaction mixture was stirred for 20 h at room temperature. The process was monitored by TLC (chloroform-methanol-water, 10:10:3). After filtration and evaporation 22.57 g (92%) of 5,6-isopropylidene ascorbic acid were obtained.

Step 2. Synthesis of 2-capryloyl-5,6-isopropylidene ascorbic acid.

Capryloyl chloride (12.0 g, 0.074 mol) was added dropwise at 0° C. to a solution of 5,6-isopropylidene ascorbic acid (14.5 g, 0.067 mol) in dry pyridine (80 mL). The reaction system was stirred for 1.5 h at 0° C. and the process was monitored by TLC (chloroform-methanol, 3:1). Afterwards the ice water (300 mL) was added and the reaction mixture was adjusted to pH 3 using phosphoric acid (~10 mL) and extracted with ethyl acetate (2×100 mL). Combined extracts were washed with saturated solution of sodium chloride up to pH 7. The washed organic layer was dried with anhydrous $MgSO_4$ and concentrated under vacuum. The residue was washed with hexane, concentrated under vacuum to give 22.9 g (89%) of 2-capryloyl-5,6-isopropylidene ascorbic acid.

Step 3. Synthesis of 2-capryloyl-3-ethyl(calcium)phosphoryl ascorbic acid.

2-Capryloyl-5,6-isopropylidene ascorbic acid (4.1 g, 0.012 mol) was dissolved in dry dichloromethane (40 mL) and triethylamine (12.4 mL, 0.122 mol) and diethylchlorophosphate (4.2 g, 0.024 mol) were added at 0° C. The process was monitored by HPLC. The reaction mixture was stirred at room temperature for 2 h, than diluted with ice water, adjusted to pH 3 with phosphoric acid (~15 mL), extracted with ethylacetate (2×100 mL) and dried with $MgSO_4$. The solvent was evaporated under vacuum and residue was dissolved in dry dichloromethane (50 mL) and than trimethylsilylbromide (2.2 g, 0.0144 mol) was added at 0° C. The solution was stirred at room temperature for 3 h and the solvent was than removed under reduced pressure. The residue was dissolved in water (30 mL) and solution was stirred vigorously for 3 h, and than adjusted by 1M water solution of calcium hydroxide up to pH 7. The solution was concentrated under vacuum and residue was crystallized from mixture methanol-water (3:2) to give 2.85 g (53%) of 2-caproyl-3-ethyl(calcium)phosphoryl ascorbic acid as white powder with the following physicochemical properties: melting point: 187–191° C. (decomp.); Composition: Calcd: C, 42.86%; H, 5.58%; P, 6.92%. $C_{16}H_{25}O_{10}PCa$. Found: C, 42.77%; H, 5.66%; P, 6.79%. $^1H$ NMR spectrum (DMSO-$d_6$/$D_2O$, 200 MHz): δ 4.50 (1H), 4.02 (1H), 3.74 (2H) (ascorbic acid unit), 1.15 (s, $CH_3$); 1.28 [(t, 3H, J 6.8 Hz, Me of OP(O)(OEt)(OCa)]; 4.12 [(dd, 2H, $CH_2$ of OP(O)(OEt)(OCa)]; 4.19–4.25 [m, 12H, $OC(O)(CH_2)_6$ ($CH_3$)]. $^{31}P$ NMR spectrum (DMSO-$d_6$/$D_2O$, 81 MHz): $δ_P$ –10.5. FAB mass spectrum m/z 448.9 ($MH^+$, $C_{16}H_{25}O_{10}PCa$, requires 448.2).

Example 2

Synthesis of 2-palmitoyl-3-diethylphosphoryl ascorbic acid

Step 1. Synthesis of 5,6-isopropylidene ascorbic acid.

20 g (0.119 mol) of anhydrous cupric sulfate were added to a suspension of 14 g (0.079 mol) of ascorbic acid in 460 mL of dry acetone. The reaction mixture was stirred for 16 h at room temperature. The process was monitored by TLC (chloroform-methanol-water, 10:10:3). After filtration and evaporation 16.3 g (95%) of 5,6-isopropylidene ascorbic acid were obtained.

Step 2. Synthesis of 2-palmitoyl-5,6-isopropylidene ascorbic acid.

Palmitoyl chloride (12.2 g, 0.0443 mol) was added dropwise at 0° C. to a solution of 5,6-isopropylidene ascorbic acid (8.7 g, 0.0403 mol) in dry pyridine (90 mL). The reaction system was stirred for 2 h at 0° C., and the process was monitored by TLC (chloroform-methanol, 3:1). The ice water (400 mL) was added and the reaction mixture was adjusted to pH 3 using phosphoric acid (~15 mL) and extracted with ethyl acetate (2×150 mL). Combined extracts were washed with saturated solution of sodium chloride up to pH 7. The washed organic layer was dried with anhydrous $MgSO_4$ and concentrated under vacuum. The residue was washed with hexane to give 16.8 g (92%) of 2-palmitoyl-5,6-isopropylidene ascorbic acid.

Step 3. Synthesis of 2-palmitoyl-3-diethylphosphoryl ascorbic acid.

2-Palmytoyl-5,6-isopropylidene ascorbic acid (7.5 g, 0.017 mol) was dissolved in dry dichloromethane (50 mL) and triethylamine (16.8 mL, 0.170 mol) and diethylchlorophosphate (4.9 g, 0.034 mol) were added at 0° C. The process was monitored by HPLC. The reaction mixture was stirred at room temperature for 2 h, than diluted with ice water, adjusted to pH 3 with phosphoric acid (~25 mL), extracted with diethyl ether (2×100 mL) to remove non-reacted reagent, and after this organic layer was dried with $MgSO_4$. The solvent was evaporated under reduced pressure and residue was diluted with 100 mL of cold water, adjusted to pH 4 with 1 M water solution of citric acid, and reaction mixture was stirred at 40° C. for 16 h. The reaction mixture was cooled to room temperature and extracted with ethylacetate (3×100 mL). Combined extracts were washed with saturated solution of sodium chloride up to pH 7. The washed organic layer was dried with anhydrous $MgSO_4$ and concentrated under vacuum. The residue was crystallized from mixture ethylacetate-hexane (1:1) to give 5.40 g (59%) of 2-palmitoyl-3-diethylphosphoryl ascorbic acid as white powder with the following physicochemical properties: melting point: 139–142° C. (decomp.); Composition: Calcd.: C, 56.73%; H, 8.55%; P, 5.64%. $C_{26}H_{47}O_{10}P$. Found: C, 56.61%; H, 8.48%; P, 5.80%. $^1H$ NMR spectrum ($CDCl_3$-MeOH-$d_4$, 200 MHz): δ 4.52 (1H), 4.01 (1H), 3.73 (2H) (ascorbic acid unit), 1.18 (s, $CH_3$); 1.25 [(t, 3H, J 6.8 Hz, Me of OP(O)$(OEt)_2$]; 1.28 [(t, 3H, J 6.8 Hz, Me of OP(O)$(OEt)_2$]; 4.13 [(ddd, 2H, $CH_2$ of OP(O)$(OEt)_2$]; 4.17 [(ddd, 2H, $CH_2$ of OP(O)$(OEt)_2$]; 4.21–4.29 [m, 28H, $OC(O)(CH_2)_{14}(CH_3)$]. $^{31}P$ NMR spectrum ($CDCl_3$-MeOH-$d_4$, 81 MHz): $δ_P$–7.3. CIMS mass spectrum m/z 550.9 ($MH^+$, $C_{26}H_{47}O_{10}P$, requires 550.4).

Example 3

Synthesis of 2-capryloyl-3-dicalciumphosphoryl-6-palmytoyl ascorbic acid

Step 1. Synthesis of 5,6-isopropylidene ascorbic acid.

9 g (0.056 mol) of anhydrous cupric sulfate were added to a suspension of 9 g (0.051 mol) of ascorbic acid in 300 mL of dry acetone and 53 mL (0.51 mol) of dry 2,2-dimethoxypropane. The reaction mixture was stirred for 10 h at room temperature. The process was monitored by TLC (chloroform-methanol-water, 10:10:3). After filtration and evaporation 10.6 g (97%) of 5,6-isopropylidene ascorbic acid were obtained.

Step 2. Synthesis of 2-capryloyl-5,6-isopropylidene ascorbic acid.

Capryloyl chloride (6.9 g, 0.042 mol) was added dropwise to a solution of 5,6-isopropylidene ascorbic acid (8.3 g, 0.038 mol) in dry dichloromethane (60 mL) and triethylamine (53 mL, 0.380 mL) at 0° C. The reaction system was stirred for 2.0 h at 0° C., and the process was monitored by TLC (chloroform-methanol, 3:1). The ice water (300 mL) was added and the reaction mixture was adjusted to pH 3 using phosphoric acid (~10 mL) and extracted with ethyl acetate (2×100 mL). Combined extracts were washed with saturated solution of sodium chloride up to pH 7. The washed organic layer was dried with anhydrous $MgSO_4$ and concentrated under vacuum. The residue was washed with hexane to give 12.1 g (92%) of 2-capryloyl-5,6-isopropylidene ascorbic acid.

Step 3. Synthesis of 2-capryloyl-3-(dicalcium)phosphoryl ascorbic acid.

2-Capryloyl-5,6-isopropylidene ascorbic acid (5.7 g, 0.017 mol) was dissolved in dry dichloromethane (50 mL) and triethylamine (17.2 mL, 0.170 mol) and diethylchlorophosphate (7.4 g, 0.051 mol) were added at 0° C. The process was monitored by HPLC. The reaction mixture was stirred at room temperature for 2 h, then diluted with ice water, adjusted to pH 3 with phosphoric acid (~15 mL), extracted with ethylacetate (2×100 mL) and dried with $MgSO_4$. The solvent was evaporated under reduced pressure and the residue was dissolved in dry dichloromethane (50 mL) and then trimethylsilylbromide (10.4 g, 0.068 mol) was added at 0° C. The solution was stirred at room temperature for 5 h and the solvent was then removed under vacuum. The residue was dissolved in water (30 mL) and the solution was stirred vigorously for 3 h, and then adjusted by 1 M water solution of calcium hydroxide up to pH 7. The solution was concentrated under vacuum crystallized from the mixture to give 3.73 g (59%) of 2-caproyl-3-(dicalcium)phosphoryl ascorbic acid.

Step 4. Synthesis of 2-capryloyl-3-(dicalcium)phosphoryl-6-palmytoyl ascorbic acid.

Palmitoyl chloride (3.1 g, 0.010 mol) was added dropwise to a solution of 2-caproyl-3-(dicalcium)phosphoryl ascorbic acid (3.5 g, 0.092 mol) in dry pyridine (40 mL) at 0° C. The reaction system was stirred for 2 h at 0° C., and the process was monitored by HPLC. The ice water (200 mL) was added and the reaction mixture was adjusted to pH 3 using phosphoric acid (~10 mL) and extracted with ethyl acetate (2×100 mL). Combined extracts were washed with saturated solution of sodium chloride up to pH 7. The washed organic layer was dried with anhydrous $MgSO_4$ and concentrated under vacuum. The residue was crystallized from mixture methanol-water (1:1) to give 3.10 g (47%) of 2-capryloyl-3-(dicalcium)phosphoryl-6-palmytoyl ascorbic acid as white powder with the following physico-chemical properties: melting point: 157–161° C. (decomp.); Composition: Calcd.: C, 51.58%; H, 7.31%; P, 4.44%. $C_{30}H_{51}O_{11}PCa_2$. Found: C, 51.72%; H, 7.51%; P, 4.60%. $^1$H NMR spectrum (DMSO-$d_6$/$D_2O$, 200 MHz): δ 4.51 (1H), 4.01 (1H), 3.75 (2H) (ascorbic acid unit), 1.15 (s, $CH_3$); 1.18 (s, $CH_3$); 4.17–4.22 [m, 12H, $OC(O)(CH_2)_6(CH_3)$]; 4.28–4.33 [m, 28H, $OC(O)(CH_2)_{14}(CH_3)$]. $^{31}$P NMR spectrum (DMSO-$d_6$/$D_2O$, 81 MHz): $δ_P$–4.9. FAB mass spectrum m/z 698.4 ($MH^+$, $C_{30}H_{51}O_{11}PCa_2$, requires 698.9).

Example 4

Synthesis of 2-glycinate-3-diethylphosphoryl ascorbic acid

Step 1. Synthesis of 5,6-isopropylidene ascorbic acid.

5,6-Isopropylidene ascorbic acid was prepared as described in example 1 (step 1).

Step 2. Synthesis of 2-glycinate-5,6-isopropylidene ascorbic acid.

Chloroacetyl chloride (1.5 g, 0.013 mol) was added dropwise at 0° C. to a solution of 5,6-isopropylidene ascorbic acid (2.16 g, 0.010 mol) in dry pyridine (50 mL). The reaction system was stirred for 1 h at 0° C., and the process was monitored by HPLC. 10 ml of 25% ammonia (water solution) were added to the reaction mixture at 0° C., the reaction system was stirred for 1 h at 0° C., and then overnight at room temperature. The reaction mixture was diluted with 500 ml of cold water; pH was adjusted to 7 with 1 M water solution of citric acid and extracted with ethyl acetate (3×100 ml). Combined extracts were washed with saturated solution of sodium chloride up to pH 7. The washed organic layer was dried with anhydrous $MgSO_4$ and concentrated under vacuum. The residue was washed with hexane, concentrated under vacuum to give 2.4 g (88%) of 2-glycinate-5,6-isopropylidene ascorbic acid.

Step 3. Synthesis of 2-glycinate-3-diethylphosphoryl-5,6-isopropylidene ascorbic acid. 2-Glycinate-5,6 -isopropylidene ascorbic acid (2.73 g, 0.010 mol) was dissolved in dry tetrahydrofurane (50 mL) and triethylamine (15.0 ml, 0.108 mol) and diethylchlorophosphate (2.6 g, 0.015 mol) were added at 0° C. The reaction process was monitored by HPLC. The reaction mixture was stirred at 0° C., and after this at room temperature for 2 h. The solvent was evaporated under reduced pressure and residue was diluted with 50 ml of cold water, adjusted to pH 4 with 1 M water solution of citric acid, and reaction mixture was stirred at room temperature for 16 h to eliminate 5,6-isopropylidene protection. The reaction mixture was washed with saturated sodium chloride and extracted with ethylacetate (3×100 ml). Combined extracts were dried with anhydrous $MgSO_4$ and concentrated under reduced pressure. The residue was crystallized from mixture ethylacetate-hexane (1:1) to give 1.89 g (51%) of 2-glycinate-3-diethylphosphoryl ascorbic acid as white powder with the following physicochemical properties. Composition: Calcd.: C, 39.02%; H, 5.42%; P, 8.40%. $C_{12}H_{20}NO_{10}P$. Found: C, 39.21%; H, 5.59%; P, 8.27%. $^1$H NMR spectrum (CDCl$_3$-DMSO-$d_6$, 200 MHz): δ 4.52 (1H), 4.01 (1H), 3.73 (2H) (ascorbic acid unit), 1.25 [(t, 3H, J 6.7 Hz, Me of $OP(O)(OEt)_2$]; 1.27 [(t, 3H, J 6.7 Hz, Me of $OP(O)(OEt)_2$]; 2.93 [(dd, 2H, $CH_2$, $CH_2NH_2$]; 3.26 [(bs, 2H, of $NH_2$]; 4.10 [(ddd, 2H, $CH_2$ of $OP(O)(OEt)_2$]; 4.15[(ddd, 2H, $CH_2$ of $OP(O)(OEt)_2$]. $^{31}$P NMR spectrum (CDCl$_3$-DMSO-$d_6$, 81 MHz): $δ_P$–3.4. CIMS mass spectrum m/z 369.5 ($MH^+$, $C_{12}H_{20}NO_{10}P$, requires 369.2).

Example 5

Dermatological Effect. Stimulation of Collagen Synthesis in Primary Human Foreskin Fibroblasts by Ascorbic acid-2-caprilate 3-monoethylphosphate The fibroblasts were placed in 24-well microculture plates in DMEM supplemented with 10% fetal calf serum containing 100 μg/ml beta-aminopropionitrile, 10 μCi [2,3-$^3$H] proline, and either ascorbic acid (AA) or ascorbic acid 2-caprilate 3-monoethylphosphate (AACP). The cultures were incubated for 24 hours. The [2,3-$^3$H]-proline incorporation into pepsine-resistant, salt precipitated extracellular collagen was determined and used as an index of efficiency by the collagen synthesis. The results were averaged from four identically treated wells and corrected for cell number in sample. The effect of AA and AACP on collagen synthesis is shown in FIG. 1. Both compounds showed the similar level of activity by stimulation of the collagen synthesis in human foreskin fibroblasts.

The invention claimed is:

1. A compound of the formula (I):

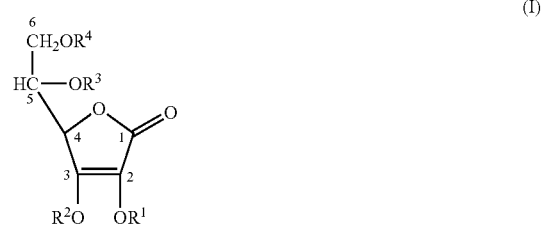

(I)

where $R^1$ is a $C_2$–$C_{22}$ saturated or unsaturated fatty acid residue, an amino acid residue, or a $C_1$–$C_{17}$ alkyl; $R^2$ is a group of the following formula (II):

(II)

wherein $R^5$ and $R^6$ are the same or different and represent hydrogen or a $C_1$–$C_4$ alkyl, or $R^5$ is a $C_1$–$C_4$ alkyl group and $R^6$ is a metal cation or ammonium cation, or $R^6$ is a $C_1$–$C_4$ alkyl group and $R^5$ is a metal cation or ammonium cation, or both $R_5$ and $R^6$ are a metal cation or ammonium cation; and $R^3$ and $R^4$ are the same or different and represent hydrogen, a $C_2$–$C_{22}$ saturated or unsaturated fatty acid residue, an amino acid residue, or a $C_1$–$C_{17}$ alkyl.

2. A process for the preparation of a compound of the formula (I):

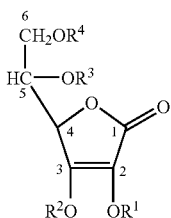

wherein $R^1$ is a $C_2$–$C_{22}$ saturated or unsaturated fatty acid residue, an amino acid residue, or a $C_1$–$C_{17}$ alkyl group; $R^2$ is a group of the following formula (II):

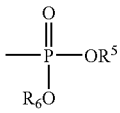

wherein $R^5$ and $R^6$ are the same or different and represent hydrogen or $C_1$–$C_4$ alkyl, or $R^5$ is a $C_1$–$C_4$ alkyl group and $R^6$ is a metal cation or ammonium cation, or $R^6$ is a $C_1$–$C_4$ alkyl group and $R^5$ is a metal cation or ammonium cation, or both $R^5$ and $R^6$ are a metal cation or ammonium cation; and $R^3$ and $R^4$ are the same or different and represent hydrogen, a $C_2$–$C_{22}$ saturated or unsaturated fatty acid residue, an amino acid residue, or a $C_1$–$C_{17}$ alkyl group, which process comprises:

(i) protecting the 5- and 6-hydroxyls of ascorbic acid to give a compound of formula (III):

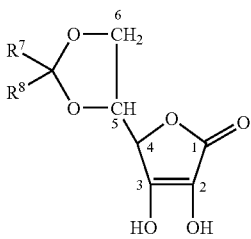

wherein $R^7$ and $R^8$ the same or different represent a $C_1$–$C_{10}$ alkyl;

(ii) reacting the resulting protected ascorbic acid of formula (III) with a compound of the formula $R^1H$ to yield a compound of formula (IV):

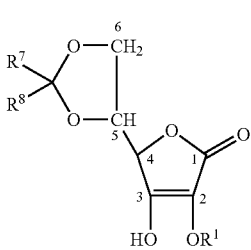

(iii) reacting the compound of formula (IV) with a phosphorylating agent to yield a compound of formula (V):

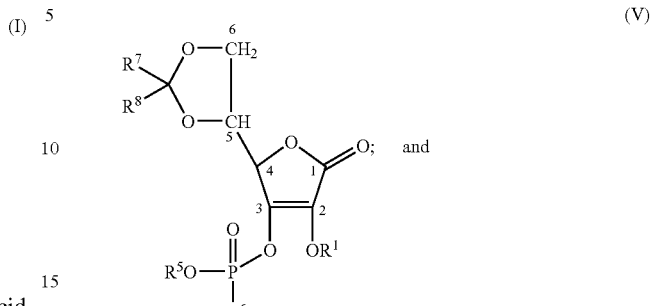

(iv) hydrolyzing the compound of formula (V) in order to deprotect the 5- and 6-hydroxyls to yield the compound of formula (I).

3. A pharmaceutical composition, comprising an effective amount of a compound of claim 1, optionally together with a pharmaceutically acceptable carrier.

4. A pharmaceutical composition according to claim 3, for treating or controlling a disease, disorder of condition associated with vitamin C deficiency.

5. A composition according to claim 3, being a topical composition and comprising a carrier suitable for application onto the skin.

6. A composition according to claim 3, being an oral composition and comprising a carrier suitable for oral administration.

7. A composition according to claim 6, formulated as capsules, tablets, microcapsules or nanoparticles encapsulating said compound.

8. A compound of claim 1 wherein $R^1$ is a $C_2$–$C_{22}$ saturated or unsaturated fatty acid residue, $R^3$ and $R^4$ are hydrogen, $R^5$ is a $C_1$–$C_4$ alkyl group and $R^6$ is a metal cation.

9. The compound of claim 8 wherein $R^1$ is capryloyl, $R^3$ and $R^4$ are hydrogen, $R^5$ is ethyl and $R^6$ is $Ca^{++}$.

10. A compound of claim 1 wherein $R^1$ is a $C_2$–$C_{22}$ saturated fatty acid residue, $R^3$ and $R^4$ are hydrogen, $R^5$ and $R^6$ each is a $C_1$–$C_4$ alkyl group.

11. A compound of claim 10, wherein $R^1$ is palmitoyl, $R^3$ and $R^4$ are hydrogen, and $R^5$ and $R^6$ each is ethyl.

12. A compound of claim 1 wherein $R^1$ is a $C_2$–$C_{22}$ saturated fatty acid residue, $R^3$ is H, $R^4$ is a $C_2$–$C_{22}$ saturated fatty acid residue and $R^5$ and $R^6$ each is a metal cation.

13. A compound of claim 12 wherein $R^1$ is capryloyl, $R^3$ is H, $R^4$ is palmitoyl, and $R^5$ and $R^6$ each is a Ca cation.

14. A compound of claim 1 wherein $R^1$ is an amino acid residue, $R^3$ and $R^4$ are hydrogen, and $R^5$ and $R^6$ each is a $C_1$–$C_4$ alkyl group.

15. A compound of claim 14 wherein $R^1$ is a glycine residue, $R^3$ and $R^4$ are hydrogen, and $R^5$ and $R^6$ each is ethyl.

16. A compound of claim 1 wherein $R^1$ is a $C_2$–$C_{22}$ saturated fatty acid residue, $R^3$ and $R^4$ are hydrogen, $R^5$ is hydrogen and $R^6$ is a $C_1$–$C_4$ alkyl group.

17. A compound of claim 16 wherein $R^1$ is a capryloyl, $R^3$ and $R^4$ are hydrogen, $R^5$ is hydrogen and $R^6$ is ethyl.

18. A cosmetic composition comprising an effective amount of a compound of claim 1, and a cosmetic acceptable carrier.

19. A cosmetic composition according to claim 18 for topical application onto the skin.

20. A cosmetic composition according to claim 19 for treatment of aging or skin dryness.

21. A compound of claim 1, wherein at least one of $R^1$, $R^3$ and $R^4$ is an amino acid residue.

* * * * *